United States Patent [19]

Gelbein

[11] 3,963,645

[45] June 15, 1976

[54] SUPPORTED METAL OXIDES

[75] Inventor: Abraham P. Gelbein, Plainfield, N.J.

[73] Assignee: The Lummus Company, Bloomfield, N.J.

[22] Filed: May 26, 1971

[21] Appl. No.: 147,159

Related U.S. Application Data

[63] Continuation-in-part of Ser. No. 803,074, Feb. 27, 1969, abandoned.

[52] U.S. Cl. .......................... 252/455 R; 252/456; 252/458; 252/464; 252/465
[51] Int. Cl.$^2$ ................... B01J 29/06; B01J 23/14; B01J 23/16
[58] Field of Search .......... 252/456, 458, 464, 465, 252/477 R, 455 R

[56] References Cited
UNITED STATES PATENTS

| | | | |
|---|---|---|---|
| 2,625,554 | 1/1953 | Darby | 252/456 X |
| 2,977,324 | 3/1961 | Dowden et al. | 252/456 X |
| 3,278,573 | 10/1966 | Kroeper et al. | 23/141 X |
| 3,371,079 | 2/1968 | Peters et al. | 252/456 X |

*Primary Examiner*—Carl F. Dees
*Attorney, Agent, or Firm*—Marn & Jangarathis

[57] ABSTRACT

A supported metal oxide wherein the metal oxide is supported on a support having a surface area greater than 50m$^2$/gm and a porosity greater than 0.4cc/gm and is supported in an amount between about 25 and about 75%, by weight, within the pores of the support. The metal oxide is generally a transition metal oxide and the supported metal oxide may be prepared by heating a mixture of the support and metal oxide to a temperature above the fusion temperature of the metal oxide, at which temperature the metal oxide is drawn into the pores of the support by capillary action. The supported metal oxide may be employed for the production of nitriles.

20 Claims, No Drawings

SUPPORTED METAL OXIDES

This application is a continuation-in-part of Application Ser. No. 803,074, filed Feb. 27, 1969 and now abandoned.

This invention relates to metal oxides and more particularly to supported metal oxides, a process for the production thereof and uses therefor.

Supported metal oxides are well-known catalysts for a wide variety of chemical reactions. In general, such catalysts are comprised of a metal oxide coated on a support material of low porosity and low surface area, commonly referred to as an inert support. The method generally employed for producing such metal oxide catalysts involves impregnating the inert support with a solution of a soluble salt of the metal oxide, separating the saturated solid and heating to remove a major portion of the solvent. The support is then calcined to convert the metal salt to the corresponding oxide. In some cases, a multiple impregnation technique is employed to achieve a higher concentration of metal oxide on the support.

Another technique employed for forming supported metal oxide catalysts involves suspending the support material in a solution of a salt of the transition metal, completely or partially evaporating the solvent and possibly mixing of the resultant material with an organic binder and pelletizing thereof. The dried pellet is then heated to an elevated temperature to effect complete dehydration and burning out of the organic material.

A further method for forming a supported metal oxide on an inert support is disclosed in U.S. Pat. No. 2,977,324 which involves contacting particles of a porous support material with the molten metal oxide to produce a catalyst in which the metal oxide is embedded in the pore structure.

U.S. Pat. 3,278,573 discloses a supported metal oxide catalyst in which the metal oxide is supported on a support of high porosity and high surface area. The catalyst, however, is prepared by an impregnation technique.

U.S. Pat. 2,838,558 discloses a supported metal oxide catalyst in which the metal oxide is supported on a heat treated activated alumina.

The supported metal oxide catalysts heretofore produced in the art, although suitable for many applications, do not possess the combination of activity, selectivity and structural strength that is desired for some applications.

Accordingly, an object of this invention is to provide a new and improved supported metal oxide.

Another object of this invention is to provide a supported metal oxide catalyst having improved activity, selectivity and structural strength.

A further object of this invention is to provide a supported metal oxide catalyst in a facile operation at low cost.

Still another object of this invention is to provide a new and improved process for producing nitriles.

These and other objects of the invention should be more readily apparent from the following detailed description thereof.

The objects of this invention are broadly accomplished by supporting the metal oxide on a support of high porosity and high surface area (an active support) in a manner such that the metal oxide is present in an amount from about 25% to about 75%, preferably from about 30% to about 60%, all by weight, substantially entirely within the pores of the support; i.e., the support is continuous in that each particle of the product has an uninterrupted lattice of the support material. Thus, the weight ratio of metal oxide to support which is substantially entirely within the pores of the support ranges from about 0.3:1 to about 3:1, preferably from about 0.4:1 to about 1.5:1. The supported metal oxide in which the metal oxide is substantially entirely within the pores of the support, as hereinafter described in more detail, is preferably prepared by contacting the support material with molten metal oxide for a time sufficient to draw the metal oxide substantially entirely within the pores of the support.

The support on which the metal oxide is to be supported has a surface area of greater than about $50 m^2/gm$ and a porosity greater than about $0.4$ cc/gm. In general, the surface area of the support is no greater than about $600 m^2/gm$ and the porosity is no greater than about $1.2$ cc/gm. Supports having a surface area of about $200 m^2/gm$ have been found to provide particularly good results. As representative examples of preferred supports having such properties, there may be mentioned: silica-alumina, zeolites, alumina, including microcrystalline and the $\gamma$, $\delta$, $\eta$, $\kappa$ and $\chi$ modifications of alumina. The surface area of the support, after placing the metal oxide substantially entirely within the pores of the support, is generally from about 5 to about $15 m^2/gm$, and in particular, about $10 m^2/gm$.

The metal oxide supported in the pores of the support may be comprised of one or more metal oxides, and as representative examples of such metal oxides, there may be mentioned oxides of the following metals; metals having atomic numbers 21 through 33, 39 through 51, 72 through 83, 57 through 71, (in particular cerium) 90 and 92. If more than one of the hereinabove noted metal oxides is used, such metal oxides may be present as discrete phases and/or such metal oxides may combine with each other whereby the metal oxides are present within the pores of the support in a combined form; i.e.; a form other than as discrete metal oxide phases. Similarly, one or more of the hereinabove noted metal oxides may be combined with a compound other than the noted metal oxides in which case such one or more metal oxides may be present in the pores in the support in a combined form; i.e., other than as a discrete metal oxide.

Thus, for example, a catalyst formed from molybdenum, phosphorous and lithium oxides may be present as discrete phases of $MoO_3$, $P_2O_5$, and $Li_2O$ or may be combined in the form of a so-called heteropolysalt [$Li_3(PMo_{12}O_{40})$] which is stoichiometrically equivalent to $Li_3PO_4 \cdot 12MoO_3$. It is to be understood that the term metal oxide as used in the specification and claims is intended to include such combined forms of metal oxides, whether combined after being placed in the pores of the support or combined externally to the support and subsequently placed into the pores of the support, with the metal oxides hereinabove described, whether as a discrete phase or in a combined form, being present in the amount specified.

In most applications wherein the supported metal oxide is to be employed as a catalyst, the particle size distribution of the support should correspond to that of the desired catalyst since the added metal oxide does not materially change the particle size of the resulting product in that the metal oxide is substantially entirely within the pores of the support. The supported metal oxides of the invention are particularly suitable for use as fluidized solids and consequently are generally produced as fine powders with a rather wide particle size distribution being preferred, generally centering in the 30 to about 200 mesh range.

The supported metal oxides are preferably prepared by thoroughly mixing a powdered metal oxide with a powdered support in the proportions desired for the final product; i.e., from about 25 to about 75%, preferably from about 30 to about 60%, all by weight, of metal oxide, until a uniform mix is obtained. The mixture is then heated to a temperature above the fusion temperature of the metal oxide, preferably in an oxygen-containing atmosphere, and maintained at this temperature while the metal oxide is drawn into the pores of the support, generally a period of time from about 1 to about 10 hours. The exact temperature employed is dependent upon the fusion temperature and fluidity of the metal oxide or mixture of metal oxides employed and on the temperature stability of the support. In general, the temperature need not be greater than about 150°C. above the fusion temperature of the metal oxide(s) and should not exceed about 1500°C.

In cases where the oxide of the metal(s) are highly refractory; i.e., have a fusion temperature greater than about 1500°C., the metal may be deposited in the pores of the support in an inert atmosphere; i.e., non-oxidizing atmosphere, as a metal salt having a fusion temperature less than about 1500°C., followed by in situ treatment to convert the salt to the metal oxide. Thus, for example, the oxides of: titanium, manganese, iron, nickel, zinc, gallium, yttrium, zirconium, tin, hafnium and tantalum have fusion temperatures about 1500°C. and these metals are deposited in the pores of the support as a salt having a fusion temperature below about 1500°C.; e.g., as the corresponding chlorides, followed by hydrolysis and calcination, in situ, to produce the metal oxide. It is also to be understood that a metal oxide or mixture of metal oxides having a fusion temperature less than about 1500°C. may also be deposited in the pores of the support as a corresponding salt, followed by appropriate treatment in situ to produce the metal oxide.

The supported metal oxides(s) may be prepared by any one of a wide variety of procedures. Thus, for example, the metal oxide(s) may be added continuously or incrementally to a preheated support, and in a particularly preferred procedure, metal oxide(s) and support are continuously added to one end of a heated kiln or similar device and supported metal oxide withdrawn from the other end thereof. The support is preferably maintained as a free flowing powder with the metal oxide(s) being drawn into the pores of the support by a capillary action.

The following Examples illustrate procedures for preparing supported metal oxides of the invention, but it is to be understood that the scope of the invention is not to be limited thereby:

EXAMPLE I

Powdered $V_2O_5$ (180 g.) was blended with 270 g. of microcrystalline gamma-alumina (Harshaw Al 1401 P, 97% $Al_2O_3$, pore volume 0.5 cc/g., surface area 200 m²/g., avg. particle size approx. 50 microns) in a rotating blender until a uniform mix was obtained (about 15 minutes mixing time required). The mixture was then heated to 695°C. in air in a muffle furnace and kept at this temperature for 3 hours. During this time, the $V_2O_5$ (m.p. 690°C.) fused and was drawn into the support. The resulting catalyst was cooled, screened, and contained 40 wt. % $V_2O_5$.

EXAMPLE II

The procedure of Example I was repeated except that the support was silica-alumina (a fluid cracking catalyst having 87% $SiO_2$, 13% $Al_2O_3$; a pore volume of 0.75 cc/g.; a surface area of 200 m²/g.; an avg. particle size of 60 microns, sold under the trademark AEROCAT) and the heating time was 5 hours.

EXAMPLE III

The procedure of Example II was repeated except that 40 wt. % $MoO_3$ was used instead of $V_2O_5$ and the fusion temperature was 800°C.

EXAMPLE IV

The procedure of Example I was repeated using 16 wt. % $V_2O_5$ and 24 wt. % $MoO_3$ as the metal oxide.

EXAMPLE V

The procedure of Example I was repeated using 24 wt. % $V_2O_5$ and 16 wt. % $MoO_3$.

EXAMPLE VI

Chromic acid ($CrO_3$) is blended with Aerocat fluid cracking catalyst (50 wt. %) and the mixture heated to 250°C. ($CrO_3$ melts at 197°C.) in air in a muffle furnace and kept at this temperature for 1 hour. The temperature is then raised to 700°C. and maintained for 3 hours to convert the $CrO_3$ in situ to $Cr_2O_3$. The resulting catalyst contains 40 wt. % $Cr_2O_3$.

EXAMPLE VII $Co(NO_3)_2.6H_2O$ is melted at 50°–60°C. and blended with Aerocat fluid cracking catalyst (53 wt. % of the cobaltous nitrate) preheated to ca. 100°C. until all the cobaltous nitrate is drawn into the pores of the support. The resulting product is then maintained at 600°C. to convert the cobaltous nitrate to cobaltic oxide ($CO_2O_3$). The resulting product is supported cobaltic oxide containing 30 wt. % of the oxide substantially entirely within the pores of the support.

EXAMPLE VIII

The procedure of Example I is repeated using 40 wt. % antimony oxide at a fusion temperature of 800°C. The resulting product contains 40 wt. % antimony oxide substantially entirely within the pores of the support.

EXAMPLE IX

Powdered cerous chloride ($CeCl_3$) is blended with Aerocat fluid cracking catalyst (43 wt. % $CeCl_3$) and the mixture heated to 850°C. ($CeCl_3$ melts at 822°C.) under a nitrogen atmosphere for 1 hour. The temperature is then increased to 1000°C. and maintained at this temperature for 3 hours in a hydrogen-containing atmosphere wherein the $CeCl_3$ is converted to cerous hydride. The temperature is then reduced to 300°C. and maintained for 3 hours in an oxygen-containing atmosphere which converts the cerous hydride to ceric oxide ($CeO_2$). The resulting product is supported ceric oxide containing 30 wt % of the oxide substantially entirely within the pores of the support.

EXAMPLE X

Powdered tungsten bromide is blended with Aerocat fluid cracking catalyst (43 wt. % tungsten bromide) and the mixture heated to 300°C. under a nitrogen atmosphere for 1 hour. The resulting product is heated to a temperature of 400°C. in a hydrogen-containing atmosphere to convert the tungsten bromide to tungsten metal which is then heated to 800°C. in an oxygen-containing atmosphere to produce the tungsten oxide. The resulting product contains 30 wt. % of the tungsten oxide substantially entirely within the pores of the support.

The preparation of the supported metal oxides(s) has been hereinabove described with respect to the preferred fusion technique. It is to be understood, however, that the scope of the invention is not to be limited thereby in that other methods for providing supported metal oxides(s) containing 25–75 wt. % metal oxide substantially entirely within the pores of the support are also possible.

The catalysts of the present invention in which the metal oxide is placed in the amounts specified into the pores of an active support are an improvement over the supported catalysts of the prior art. Thus, for example, the catalysts of the present invention are an improvement over those in which the metal oxide is placed in the pores of a support of low porosity and low surface area (an inert support), such as alpha-alumina. The catalysts of the present invention are also an improvement over those in which a metal oxide is impregnated on an active support. The catalysts of the present invention are unexpectedly more active than prior art supported catalysts, as evidenced by both improved selectivity and conversion, as hereinafter noted in Example XII. These results are considered to be particularly unexpected in that on the basis of prior art knowledge, it would be expected that the use of a fusion technique would mask the support and derogate from any benefit which would be expected to result from the use of an active support.

The supported metal oxides of the invention are quite distinct from those heretofore known in the art in that they have improved catalyst activity, selectivity and improved structural strength. Although the invention is not to be limited by any theoretical reasoning, it is believed that such improvements result from the fact that unlike previous supported metal oxides the metal oxide is present as a deep continuous film on a continuous support, permitting free migration of oxygen and/or electron "holes" or electrons to and from the surface. The supported metal oxides prepared by simple impregnation techniques do not contain the high concentration of metal oxides which are present in the supported metal oxides of the present invention; i.e., the prior art supported metal oxides contain less than 25% metal oxide, and therefore have thin and/or discontinuous films of the metal oxide, resulting in poor electron migration and incomplete coverage of the support. The supported metal oxides prepared by a multiple impregnation technique still do not contain the high metal oxide concentrations of the invention and in addition the interface between metal oxide layers offers resistance to electron migration.

The supported metal oxides produced by these impregnation techniques, have a lower attrition resistance than the supported metal oxides of the invention because the former have a high content of metal oxide on the outside surface of the support. This is particularly disadvantageous in that the attrition causes intolerable pressure drop in static beds and loss of fines in exit gases from fluidized beds.

The supported metal oxides of the invention may be employed in any one of a wide variety of chemical reactions. Thus, for example, the supported metal oxides of the invention; in particular the oxides of the following metals: thorium, uranium, bismuth, molybdenum, titanium, vanadium, tin, chromium, tungsten, cobalt, iron, manganese, copper, arsenic, antimony, etc., may be employed for the production of nitriles, in particular aromatic nitriles from alkyl substituted aromatic hydrocarbons and aliphatic nitriles from olefinically unsaturated aliphatic hydrocarbons.

The hydrocarbon is contacted with ammonia in the vapor phase in the presence of the supported metal oxide, either in the absence or presence of a free-oxygen-containing gas, preferably in the absence of oxygen. The contacting is generally effected at temperatures from about 300°C. to about 500°C., preferably from about 350°C. to about 450°C., with the contact time generally ranging from about 0.1 to about 10 seconds, preferably from about 0.5 to about 2 seconds. The reaction pressures generally range from about 1 to about 5 atmospheres. The mole ratio of ammonia to hydrocarbon generally ranges from about 1:1 to about 10:1, preferably from about 2:1 to about 5:1. If an oxygen-containing gas is employed in the feed, the gas is employed in an amount such that the quantity of oxygen and hydrocarbon in the feed is outside the explosive range. It is to be understood that the hereinabove described conditions are only illustrative and the choice of optimum conditions will vary with the particular reactants and supported metal oxide. The choice of optimum conditions is considered to be within the scope of those skilled in the art.

In accordance with a preferred embodiment, the hydrocarbon and ammonia are contacted in the absence of oxygen and the supported metal oxide is employed in a fluidized condition. In the preferred embodiment, the supported metal oxide is periodically passed to another reactor (in general the supported metal oxide is not maintained on-stream for a period greater than 30 minutes, preferably from about 2 to about 10 minutes) and contacted therein with a free-oxygen-containing gas for a period of time ranging from about 2 to about 20 minutes. The supported metal oxide is then recycled to the nitrile production zone. Although Applicant does not intend to limit the invention by theoretical reasoning, it is believed that the supported metal oxide is reduced during the nitrile production step and consequently periodic oxidation thereof is required to maintain the supported metal oxide in the oxidized form necessary for the nitrile production.

The hydrocarbon starting material may be an alkyl substituted aromatic hydrocarbon, with the aromatic nucleus being either benzene or naphthalene, and in particular benzene, and may contain two or more alkyl groups in which case the resulting product is a polynitrile. The alkyl group generally contains no more than 4 carbon atoms, preferably no more than 2 carbon atoms. As representative examples of suitable alkyl substituted aromatic hydrocarbons there may be mentioned: toluene; the various xylenes to produce the various phthalonitriles; ethyl benzene; trimethyl benzenes; methyl naphthalenes; and the like. It is to be understood that a mixture of such compounds may be employed in which case the reaction effluent contains a mixture of nitriles. The hydrocarbon starting material may also be an olefinically unsaturated aliphatic hydrocarbon, in particular propylene and isobutylene, in which case the products are acrylonitrile and methacrylonitrile, respectively.

The invention is further illustrated by the following Examples but the scope of the invention is not to be limited thereby.

EXAMPLE XI

The feeds tabulated below were contacted in the presence of 75 g. –90 g. of the supported metal oxides of Examples I and II through V at temperatures of 430°C. –460°C. and a contact period of 0.6 seconds. In Case I, oxygen was present in the feed gas while in Case II, the feed was free of oxygen, with the metal oxide being periodically regenerated in a separate zone by contact with an oxygen-containing gas.

|  | p-xylene | Ammonia, mole % | $O_2$ | $N_2$ | $H_2O$ |
|---|---|---|---|---|---|
| Case I | 4.2 | 17.2 | 8.6 | 32.4 | 37.8 |
| Case II | 4.3 | 17.0 | — | 68.1 | 10.6 |

| Catalyst | Case | Conversion Mol. % | *Space Yield lb. TPN/hr-lb cat. | Selectivity to terephthalonitrile and p-tolunitrile |
|---|---|---|---|---|
|  |  |  |  | Mol. % |
| I | I | 54 | 0.35 | 87 |
|  | II | 63 | 0.43 | 84 |
| III | I | 29 | 0.17 | 80 |
| IV | I | 40 | 0.26 | 86 |
|  | II | 46 | 0.31 | 85 |
| V | II | 34 | 0.23 | 85 |

*Total nitrile groups produced, calculated as terephthalonitrile.

The results indicate that reaction in the absence of oxygen results in higher conversion and productivity without decrease in yield.

EXAMPLE XII

A. A catalyst was prepared as described in Example I of this application, except that the support is alpha-alumina.

B. A catalyst having 10 wt. % $V_2O_5$ impregnated on the support of Example I of this application was prepared by the impregnation technique of Example I of U.S. Pat. No. 2,838,558 (the active support was not heat treated).

A feed comprised of 4.3 mole % p-xylene, 17.0 mole % ammonia; 68.1 mole % nitrogen; and 10.6 mole % water, is contacted with 75 grams of the supported metal oxides, designated A and B above and the supported metal oxide of Example I at a temperature of 850°F. and a contact time of 0.6 seconds. The results were as follows:

|  | Conversion Mol. % | Space Yield lb. TPN/hr-lb cat. | Selectivity to terephthalonitrile and p-tolunitrile |
|---|---|---|---|
| A | 26 | 0.13 | 61 |
| B | 22.3 | 0.12 | 68 |
| Ex. I | 63 | 0.43 | 84 |

The results indicate that a supported metal oxide of the present invention in which the metal oxide is placed substantially entirely within the pores of an active support provides improved conversion and selectivity as compared to both a metal oxide impregnated on an identical support and a metal oxide placed substantially entirely within the pores of an inert support.

The supported catalysts of the present invention provided improved results in the production of nitriles as a result of their superior activity. Thus, the catalysts of the present invention are effective for the production of nitriles in the absence of oxygen, which permits greater flexibility in that there is no possibility of explosive mixtures. In addition, in accordance with the present invention, nitriles can be effectively produced at lower ammonia to hydrocarbon feed ratios; i.e., the prior art indicates that the use of an active support requires ammonia to hydrocarbon feed ratios of around 20:1, whereas, in accordance with the present invention, nitriles can be produced at ammonia to hydrocarbon feed ratios in the order of 4:1.

The supported metal oxides of the invention may be used for any of a wide variety of purposes generally known in the art. Thus, for example, as hereinabove noted supported metal oxides may be employed in the production of nitriles. In addition, supported metal oxides are useful as catalysts in dehydrogenation reactions and/or oxidation reactions and/or hydrogenation reactions. Thus, for example, the supported oxides of vanadium, silver, copper, manganese, nickel, molybdenum and tungsten may be employed for the production of: olefin oxides (ethylene to ethylene oxide); anhydrides (butene to maleic anhydride; o-xylene to phthalic anhydride); and carboxylic acids (propylene to acrylic acid) and the supported oxides of chromium, zinc, manganese, iron, copper, zirconium, cerium and cobalt may be employed for the production of olefinically unsaturated compounds (propane to propene; butene to butadiene; ethyl benzene to styrene). The supported metal oxides of the invention may be employed in a manner identical to those supported metal oxides heretofore known in the art and therefore no detailed discussion of such uses is deemed necessary for a full understanding of the invention.

Numerous modifications and variations of the present invention are possible in light of the above teachings and therefore the invention may be practiced otherwise than as particularly described.

What is claimed is:

1. A composition of matter comprising:
    a metal oxide selected from the group consisting of vanadia, molybdena, and mixtures thereof, supported on a porous support selected from the group consisting of silica-alumina and gamma-alumina, said metal oxide being present in an amount to provide a metal oxide to support weight ratio ranging from about 0.3:1 to about 3:1 substantially entirely within the pores of the support, said metal oxide having been placed in molten form substantially within the pores of a support having a surface area greater than about 50 meter square per gram and a porosity greater than about 0.4cc per gram.

2. The composition of claim 1 wherein said support is gamma-alumina.

3. The composition of claim 2 wherein the metal oxide is vanadia.

4. The composition of claim 1 wherein said support is silica-alumina.

5. The composition of claim 4 wherein said metal oxide is vanadia.

6. The composition of claim 1 wherein said metal oxide is vanadia and said support is gamma-alumina having a surface area of about 200 meters square per gram.

7. The composition of claim 1 wherein said metal oxide is vanadia and said support is silica-alumina having a surface area of about 200 meters square per gram.

8. A composition of matter comprising:
a supported metal oxide having a surface area from about 5 to 15 meter square per gram, said metal oxide being selected from the group consisting of vanadia, molybdena, and mixtures thereof, said metal oxide being substantially, entirely within the pores of a support selected from the group consisting of gamma-alumina, and silica-alumina, said metal oxide being present in an amount to provide a weight ratio of metal oxide to support from about 0.3:1 to about 3:1, said metal oxide having been placed in molten form substantially, entirely, within the pores of a support having a surface area greater than about 50 meter square per gram and a porosity greater than about 0.4cc per gram.

9. The composition of matter of claim 8 wherein said metal oxide to support weight ratio is from about 0.4:1 to 1.5:1.

10. The composition of claim 8 wherein said support is gamma-alumina.

11. The composition of claim 10 wherein said metal oxide is vanadia.

12. The composition of claim 10 wherein said metal oxide is a mixture of vanadia and molybdena.

13. The composition of claim 8 wherein said support is silica-alumina.

14. The composition of claim 13 wherein said metal oxide is vanadia.

15. The composition of claim 13 wherein said metal oxide is a mixture of vanadia and molybdena.

16. A process for producing a supported metal oxide comprising:
mixing at least one member selected from the group consisting of the oxides and salts of vanadium and molybdenum with a support having a surface area greater than about 50 meter square per gram and a porosity greater than about 0.4cc per gram, said support being selected from the group consisting of gamma-alumina and silica-alumina, said member having a fusion temperature no greater than about 1500°C and being mixed in an amount to provide from about 25% to about 75%, by weight, metal oxide in the final product, heating the mixture to a temperature above the fusion temperature of the salt whereby the member is drawn substantially, entirely into the pores of the support and further treating the supported member when the member is a metal salt to convert the salt to the metal oxide.

17. The process of claim 16 wherein the support is silica-alumina.

18. The process of claim 17 wherein said member is vanadium oxide.

19. The process of claim 16 wherein said support is gamma-alumina.

20. The process of claim 19 wherein said member is vanadium oxide.

* * * * *